United States Patent
Feng et al.

(10) Patent No.: US 7,533,577 B1
(45) Date of Patent: *May 19, 2009

(54) DETERMINATION OF ELASTOMER MATERIAL PROPERTIES FOR THE MULLINS EFFECT USING A BI-AXIAL TEST DEVICE

(75) Inventors: William W Feng, Lafayette, CA (US);
John O. Hallquist, Livermore, CA (US)

(73) Assignee: Livermore Software Technology Corporation, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/025,036

(22) Filed: Feb. 3, 2008

Related U.S. Application Data

(63) Continuation-in-part of application No. 11/746,039, filed on May 8, 2007.

(51) Int. Cl.
  *G01N 3/10* (2006.01)
  *G01D 1/16* (2006.01)
(52) U.S. Cl. .................. 73/789; 73/150 A; 73/840; 73/794; 73/37
(58) Field of Classification Search .......... 73/838, 73/840, 788, 789, 791, 794, 798, 37, 37.5, 73/37.6, 37.7, 37.8
See application file for complete search history.

(56) References Cited

U.S. PATENT DOCUMENTS

| | | | |
|---|---|---|---|
| 1,819,719 A * | 8/1931 | Schopper et al. .............. 73/805 |
| 3,580,050 A   | 5/1971 | Waldron |
| 3,817,109 A * | 6/1974 | Audet et al. ............... 73/865.6 |
| 4,140,556 A * | 2/1979 | Baba et al. .................. 148/418 |
| 4,159,217 A * | 6/1979 | Selines et al. ................ 148/577 |
| 6,267,011 B1 * | 7/2001 | Kurtz et al. ................... 73/789 |
| 6,349,588 B1 * | 2/2002 | Brown et al. ................... 73/37 |
| 7,013,709 B2 * | 3/2006 | Hajduk et al. .................. 73/37 |

(Continued)

OTHER PUBLICATIONS

R. Johannknecht, G. Clauss, and S. Jerrams. "Determination of non-linear, large, equal biaxial stresses and strains in thin elastomeric sheets by bubble inflation." Proc Instn Mech Engrs J Materials: Design and Applications Part L. vol. 216. (2002) pp. 233-243.*

(Continued)

*Primary Examiner*—Lisa M Caputo
*Assistant Examiner*—Punam Patel
(74) *Attorney, Agent, or Firm*—Roger H. Chu

(57) ABSTRACT

Systems and methods for determining material properties of elastomers for the Mullins effect are described. In one aspect of the present invention, material properties of an elastomer membrane specimen are obtained using a system comprising a bi-axial test device, a pump, a fluid reservoir, a linear variable differential transformer, a pressure transducer and a computer. The bi-axial test device comprises a top plate and a bottom plate. The top plate has an elliptical shape hole configured to allow the specimen to be expanded up by pressures of the inflating fluids. The hole is so dimensioned that the specimen can be expanded with a relatively low pressure. The bottom plate is a solid plate configured with a fluid intake at one side and a fluid outlet at the other end. The fluid intake is connected to the fluid reservoir. Fluids stored in the fluid reservoir are pumped into the bi-axial test device by the pump. The fluid outlet is connected to the pressure transducer.

15 Claims, 13 Drawing Sheets

U.S. PATENT DOCUMENTS 7,472,602 B1     1/2009     Feng et al.
2006/0270023 A1*   11/2006   LeDuc et al. ............ 435/289.1

OTHER PUBLICATIONS

USPTO—1st Office Action mailed Aug. 29, 2008 (U.S. Appl. No. 11/746,039).

Applicants' Response to the 1st Office Action (U.S. Appl. No. 11/746,039) Filed Sep. 10, 2008.

H. K. Rasmussen, J. H. Christensen, S. Gottsche, "Inflation of polymer melts into elliptic and circular cylinders," Journal of Non-Newtonian Fluid Mechanics 93 pp. 245-263. 2000.

N. Reuge, F. M. Schmidt, Y. Le Maoult, M. Rachik, F. Abbe, "Elastomer Biaxial Characterization Using Bubble Inflation Technique, I: Experimental Investigations." Polymer Engineering and Science, Mar. 2001, vol. 41, No. 3, pp. 522-531.

USPTO—Notice of Allowance mailed Nov. 28, 2008 (U.S. Appl. No. 11/746,039).

* cited by examiner

DETERMINATION OF ELASTOMER MATERIAL PROPERTIES FOR THE MULLINS EFFECT USING A BI-AXIAL TEST DEVICE

CROSS-REFERENCE TO RELATED APPLICATIONS

This application is a continuation-in-part of co-pending U.S. patent application Ser. No. 11/746,039 for "Determination of elastomer material properties for the Mullins effect using a bi-axial test device", filed on May 8, 2007.

FIELD OF THE INVENTION

The present invention generally relates to determination of rubber-like material properties, more particularly to methods and systems for determining the material properties of elastomers for the Mullins effect using a bi-axial test device.

BACKGROUND OF THE INVENTION

Rubber-like materials such as elastomers have been used in many parts and structures in various industries (e.g., automotive, aerospace, etc.) for years. But the mechanical properties (e.g., stress-strain or stress-stretch ratio relationship) of elastomer, other than the elastic properties, are still not clearly defined; hence, designs and analyses (especially used in computer-aided engineering) of these structures are generally based on the elastic properties of the elastomer only. In reality, elastomers exhibit non-elastic effects such as the Mullins effect, viscoelastic, and chronorheological behavior, and the magnitudes of the non-elastic properties are often large enough that they should not be neglected.

Elastomer in its virgin state exhibits a relatively stiffer response on the initial loading. When the elastomer is loaded, subsequently unloaded, then reloaded, the stress-strain relationship follows a significantly softer path. After several unloading-reloading cycles, the stress-strain relationship stabilizes, and additional unloading-reloading cycles retrace the stabilized path in the stress-strain curve. The non-elastic material behavior of elastomer described herein is referred to as the Mullins effect, in which the stress-strain relationship depends on the maximum loading previously encountered.

To date, very few analytical and experimental studies for determining non-elastic properties of elastomers have been attempted. This is because the study of mechanics for elastomers must consider both geometric and material nonlinearities. The additional effects and the lack of an adequate constitutive equation that describes these phenomena make the analytical and experimental studies very difficult.

The determination of the material properties is generally conducted using uni-axial test, as shown in FIG. 1A, in which an elastomer specimen 102 is pulled by a uni-axial tension 104 (i.e., one-dimensional test) at either end. However, the material properties obtained from the one-dimensional test may not represent true behaviors of elastomer contained in a structure, which is generally not in a one-dimensional space. To solve this deficiency, one of the prior art attempts is to stretch a sheet of an elastomer specimen (membrane) 112 in two planar directions as shown in FIG. 1B. The specimen 112 is pulled by equal tensions 114 in both of the specimen's planar axes. However, this prior art approach requires a huge piece of specimen (thereby huge laboratory) to avoid the edge effects from point loads (i.e., tensions 114) applied around the perimeter. This is not a practical solution because the test would have to be conducted in a very large test facility or laboratory.

Further, the current or prior art numerical equations (i.e., constitutive equations) are not adequate to represent true behaviors of elastomers. One of the prior art constitutive equations is the Ogden equation, which suggests or assumes the loading and subsequent reloading paths are the same. The Ogden equation does not represent the true behaviors of elastomers, which become softer in a subsequent reloading path than in the original loading path.

The elastomer behaviors as shown in FIG. 2 are calculated using the Ogden equation. In FIG. 2, the vertical axis represents stress in the elastomer. The horizontal axis represents the stretch ratio $\lambda$ of the elastomer. The stretch ratio is defined as the stretched length divided by the original length of the elastomer. Therefore, the relationship between the stretch ratio $\lambda$ and the strain $\epsilon$ is that $\epsilon = \lambda - 1$. The elastomer is first loaded following the path 202 starting at un-stretched position 201 (i.e., stretch ratio equal to one) until the stretch ratio reaches four (4) at 203. Then the elastomer is unloaded following a first unload path 204 back to the origin 201. Next the elastomer is reloaded following the reloading path 212 to a stretch ratio about 5.5 at 213. The first portion of the reloading path 212 is assumed to be the same as the original loading path 202 in the Ogden equation. It is emphasized that this is an incorrect assumption thus leading to inaccurate numerical analysis of elastomers. Finally the elastomer is unloaded again at 213. Based on the Ogden equation, the elastomer follows the second unloading path 214 back to the origin 201.

Given the foregoing drawbacks, problems and limitations of the prior art, it would be desirable to have improved methods and systems to determine material properties of elastomers such that the more correct behaviors of elastomers such as the Mullins effect can be numerically calculated and analyzed.

BRIEF SUMMARY OF THE INVENTION

This section is for the purpose of summarizing some aspects of the present invention and to briefly introduce some preferred embodiments. Simplifications or omissions in this section as well as in the abstract and the title herein may be made to avoid obscuring the purpose of the section. Such simplifications or omissions are not intended to limit the scope of the present invention.

The present invention discloses systems and methods to determine material properties of elastomers for the Mullins effect using a bi-axial test device. According to one aspect of the present invention, material properties of an elastomer membrane specimen are obtained using a material properties determination system including a first bi-axial test device, a pump, a fluid reservoir, a linear variable differential transformer (LVDT), a pressure transducer and a computer. The first bi-axial test device comprises a top plate and a bottom plate. The top plate has a circular hole configured to allow the specimen to be expanded up by pressures of the inflating fluids. The circular hole or opening is so dimensioned that the specimen can be expanded with a substantially low pressure (e.g., less than 15 pound-force per square inch (psi)). The bottom plate is a solid plate configured with a fluid intake at one side and a fluid outlet at the other end. The fluid intake is connected to the fluid reservoir. Fluids stored in the fluid reservoir are pumped into the first bi-axial test device by the pump. The fluid outlet is connected to the pressure transducer.

The elastomer membrane specimen has a uniform thickness and a large enough size to be sandwiched between the top and bottom plates for forming a fluid-tight seal, when the top and bottom plates are coupled together with a plurality of connector means (e.g., screws). The amount of the pressure in the first bi-axial test device is measured by the pressure transducer, while the inflated vertical displacement at the center of the specimen (i.e., center of the circular hole) is measured by the LVDT. Both the measured vertical displacement and the pressure are gathered and plotted in a computer. Since the pressure is uniformly distributed inside the inflated membrane specimen, the tensions at the center of the membrane specimen are equal in two planar directions (i.e., bi-axial tension). The size of the circular hole is relatively small with a radius between 1-2 inches.

In another aspect of the present invention, a new constitutive equation with separate loading, unloading and subsequent reloading paths is created. Two sets of material constants of the new constitutive equation for the unloading and reloading paths are calculated using least square fitting techniques based on the respective measured data from a bi-axial test. The new constitutive equation can be programmed in a computer aided engineering analysis software application such as finite element analysis software. As a result, the Mullins effect can be numerically analyzed for structure containing elastomers using the new constitutive equation including the measured data from the bi-axial test.

According to yet another aspect of the present invention, instead of the first bi-axial test device, the material properties determination system may use a second bi-axial test device. Most of the components of the second bi-axial test device are same as or substantially similar to those of the first bi-axial test device. The difference is that a top plate has an elliptical hole or opening. Due to the elliptical shape, tensions at the center of the membrane specimen are not equal in two planar directions any more. The bi-axial tensions are function of the vertical displacement of the specimen by the inflating fluids. It is noted that the first bi-axial test device is a special case of the more generic second bi-axial test device.

According to one embodiment, the present invention is a bi-axial test device for determining elastomer material properties for the Mullins effect under bi-axial tension, the device comprises at least the following: a top plate having a circular opening, the circular opening having a diameter; a bottom plate having an inflating fluid intake and an inflating fluid outlet; and a plurality of connecting means for coupling the top and bottom plate.

According to another embodiment, the present invention is a system for determining elastomer material properties for the Mullins effect under bi-axial tension, the system comprises at least the following: a bi-axial test device having an the inflating fluid intake and an inflating fluid outlet; a fluid reservoir coupling to the inflating fluid intake providing inflating fluids; and a pump, coupling to the fluid reservoir, configured to control the inflating fluids. The system further comprises the following: a linear variable differential transformer (LVDT) configured to measure vertical displacement at the center of an elastomer specimen placed in the bi-axial test device; a pressure transducer, coupling to the inflating fluid outlet, configured to measure pressure of the inflating fluids; and a computer, coupling to the LVDT and the pressure transducer, configured to gather the measured pressure and displacement.

According to yet another embodiment, the present invention is a method for numerically analyzing structure containing elastomer, the method comprises at least the following: conducting a bi-axial tension test of a specimen of the elastomer using a bi-axial test device of an elastomer material properties determination system, wherein the bi-axial tension test comprises loading, unloading and reloading phases; plotting measured pressure versus vertical displacement curve include the loading, unloading and reloading phases; determining a first set of material constants by a least square fitting technique using the measured pressures and displacements in the unloading phase; and determining a second set of material constants by least square fitting technique using the measured pressures and displacements in the reloading phase; and numerically analyzing the structure using a constitutive equation that uses the first and the second sets of material constants to describe behaviors of the elastomer.

One of the objects, features, and advantages of the present invention is to allow determination of elastomer material properties using a bi-axial test device in a relatively compact laboratory for various ratios of bi-axial tension. Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

DETAILED DESCRIPTION

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the present invention are discussed herein with reference to FIGS. 3A-5. However, those skilled in the art will readily appreciate that the detailed description given herein with respect to these figures is for explanatory purposes as the invention extends beyond these limited embodiments.

Figure 1A:
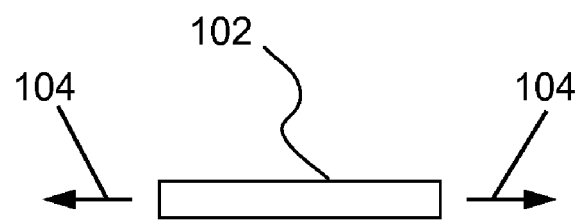
FIG. 1A is a diagram showing an elastomer stick specimen under uni-axial tension.
Figure 1B:
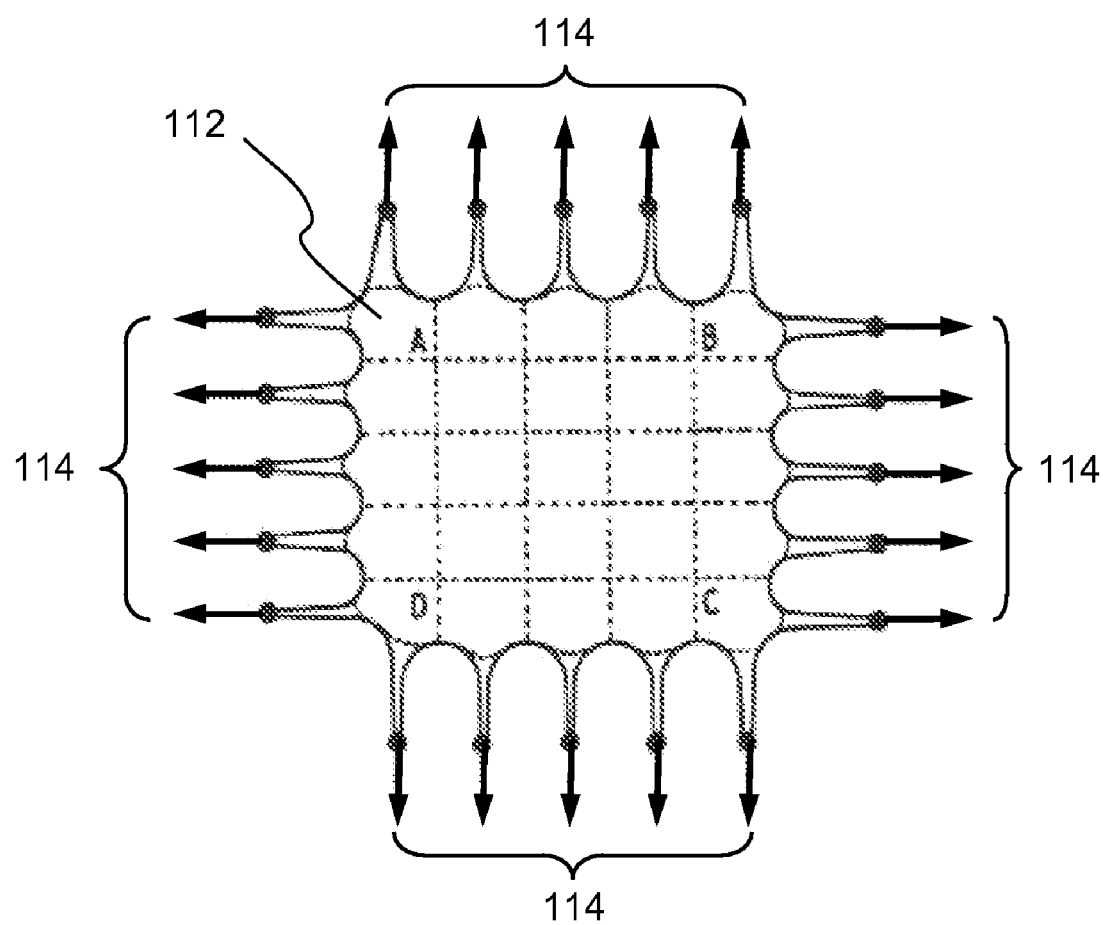
FIG. 1B is a diagram showing a sheet of elastomer membrane specimen under bi-axial tension based on a prior art solution.
Figure 2:
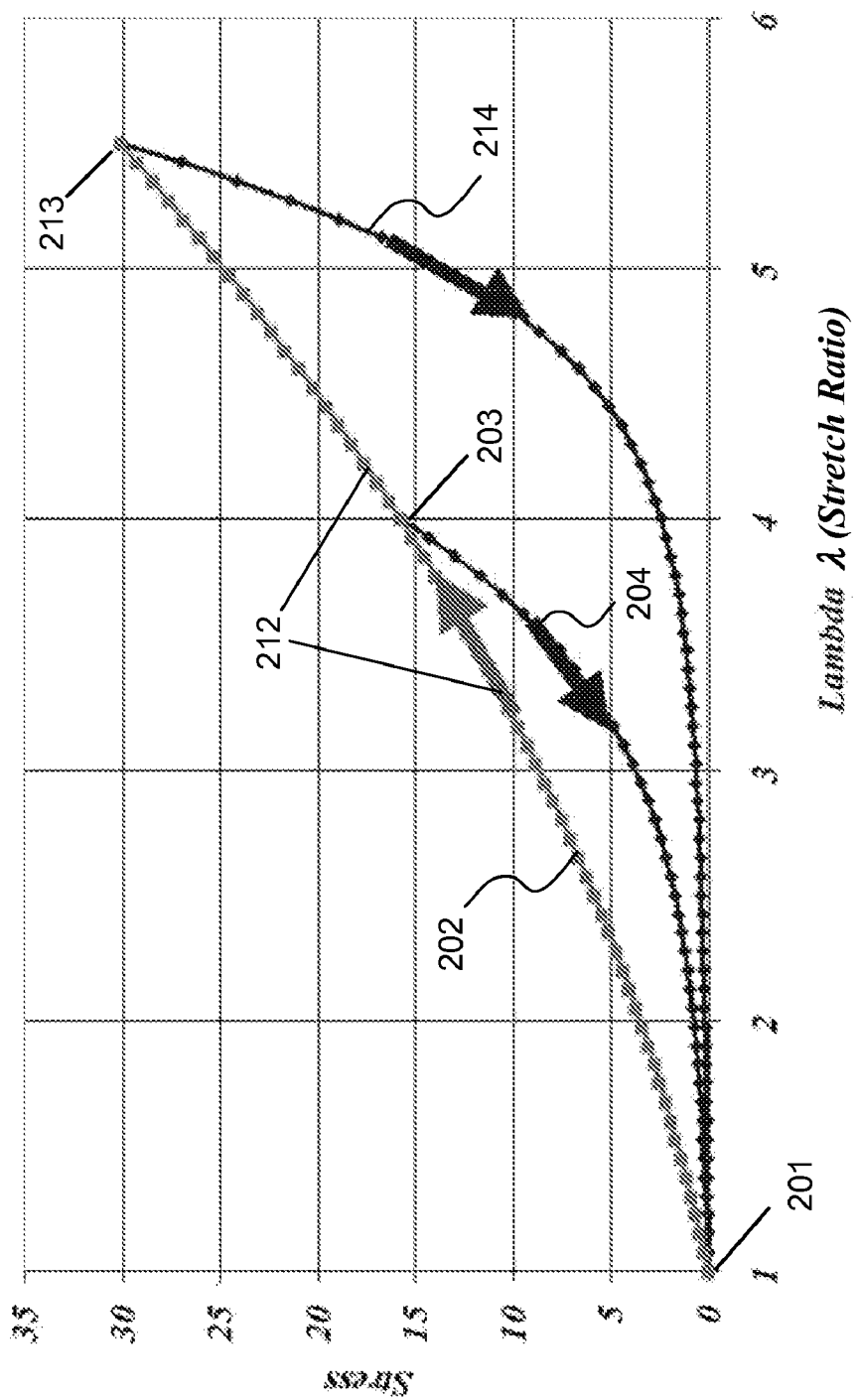
FIG. 2 is a diagram showing the stress-stretch ratio relationship of an elastomer under load-unload-reload phases calculated using the Ogden constitutive equation—a prior art approach.
Figure 3A:
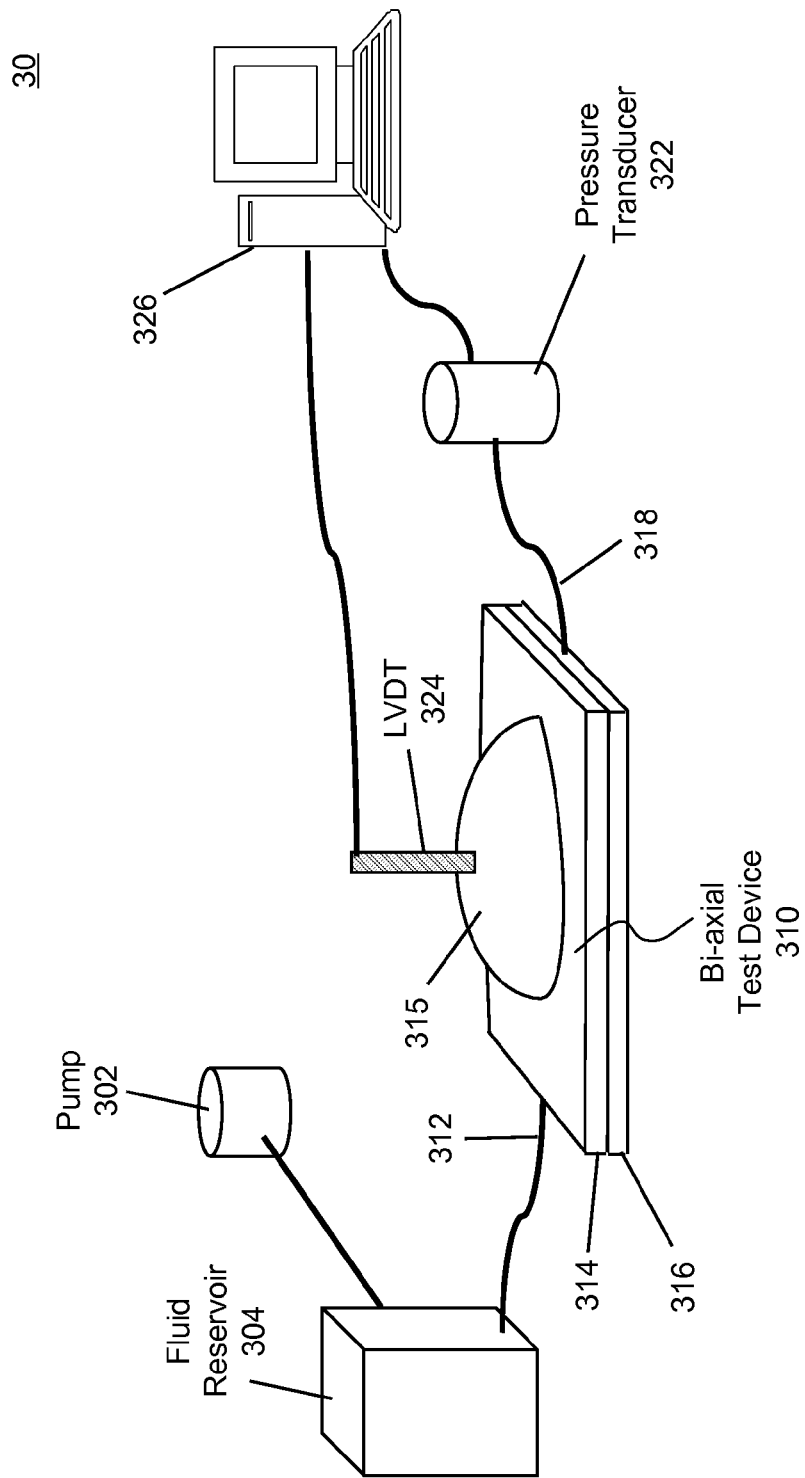
FIG. 3A is a diagram depicting an exemplary elastomer material properties determination system including a first exemplary bi-axial test device, according to an embodiment of the present invention.

Referring now to the drawings, in which like numerals refer to like parts throughout several views. FIG. 3A depicts an exemplary elastomer material properties determination system 30 including a first exemplary bi-axial test device 310, according to an embodiment of the present invention. The system 30 comprises an inflating fluid subsystem and a data measurement subsystem, both coupling to the first bi-axial test device 310. The first bi-axial test device 310 comprises a top plate 314 and bottom plate 316. The top plate 314 includes a circular hole. The bottom plate 316 is a solid plate coupled with an inflating fluid intake 312 and with an inflating fluid outlet 318. An elastomer membrane specimen 315 is placed between the top plate 314 and the bottom plate 316 during a bi-axial tension test. The inflating fluid subsystem comprises a fluid reservoir 304 and a pump 302. The pump 302 is used for pumping inflating fluids (e.g., air or water), from the fluid reservoir 304 to the first bi-axial test device 310, to inflate, deflate and re-inflate the elastomer membrane specimen 315. The data measurement subsystem includes a computer 326, a linear variable differential transformer (LVDT) 324 and a pressure transducer 322. The pressure transducer 322, coupling to the first bi-axial test device 310 via the inflating fluid outlet 318, is configured to measure pressures of the inflating fluids throughout the bi-axial test. The LVDT 324 is configured to measure vertical displacement at the center of the elastomer membrane specimen 315 during the bi-axial test. Both the pressure transducer 322 and the LVDT 324 are coupled to the computer 326 (e.g., personal computer, server, laptop, desktop), which gathers and plots the measured data (i.e., pressure and displacement). The pump 302 is optionally configured to be controlled by the computer 326.

Figure 3B:
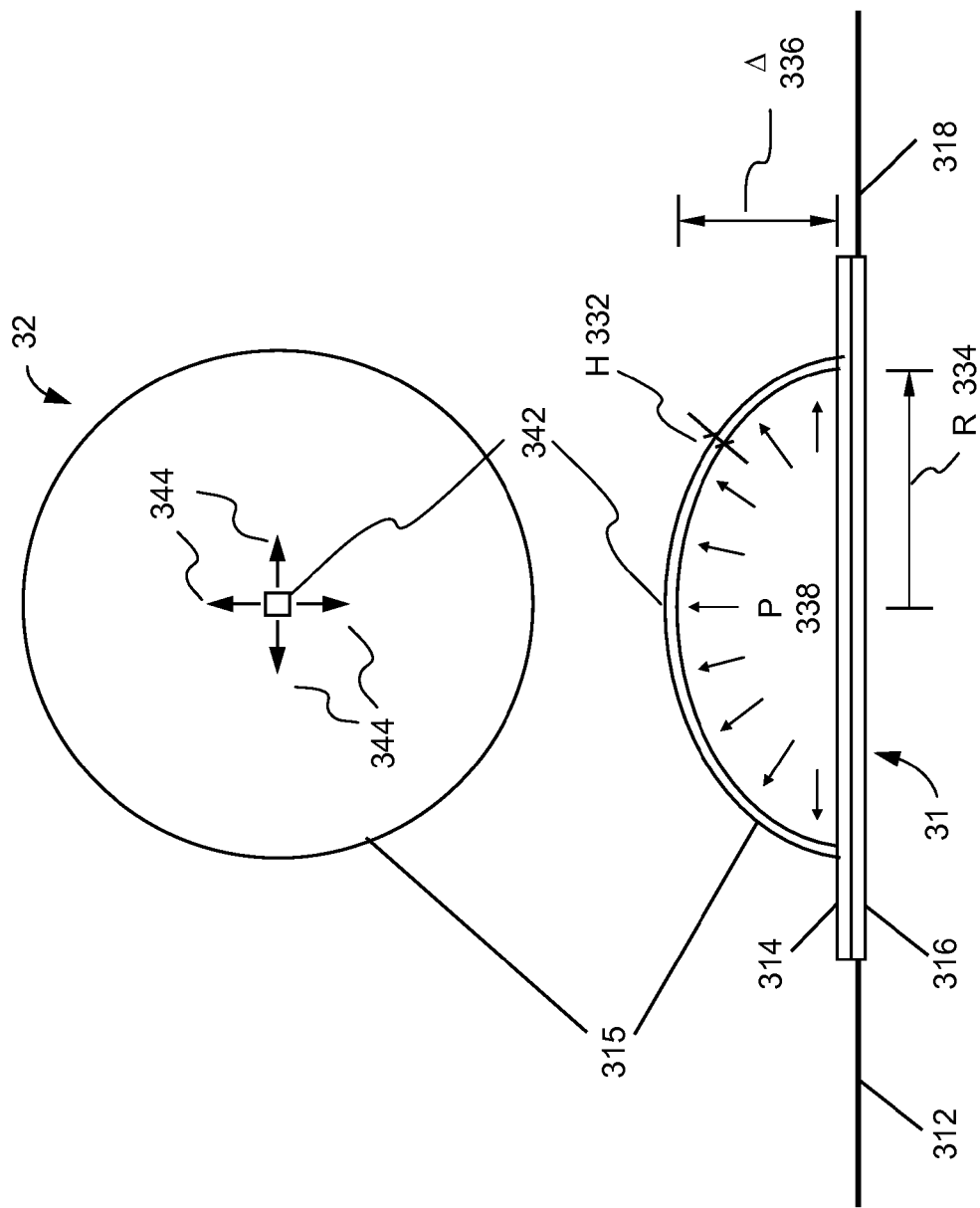
FIG. 3B is a diagram showing a lateral elevation view of the first exemplary bi-axial test device of FIG. 3A and a top plan view of the elastomer membrane specimen in accordance with one embodiment of the present invention.

FIG. 3B shows a lateral elevation view 31 of the first bi-axial test device 310 and a top view 32 of the elastomer membrane specimen 315 of FIG. 3A, according to an embodiment of the present invention. The elastomer specimen 315 has a uniform thickness H 332. As shown in the lateral view 31, the elastomer membrane specimen 315 is expanded up to a vertical displacement Δ 336 at the center 342 by a pressure 338 from the inflating fluids. The circular hole or opening of the top plate 314 has a radius R 334. The top view 32 shows that the membrane 315 at the center 342 is subjected to equal bi-axial tensions 344 as the elastomer membrane 315 is being expanded upwards by the pressure of the inflating fluids.

Sometime, a stiffer material will require higher inflating pressure, which may present a technical problem to achieve the higher pressure in a laboratory. The simplest way to solve this problem is to use either a larger size or a thinner specimen, for example, a membrane, doubled the size of radius or halved the thickness, will require one-half of the pressure to achieve a same vertical displacement. In one embodiment, typical size of the circular hole is relatively small with a radius between one to two inches.

Figure 3C:
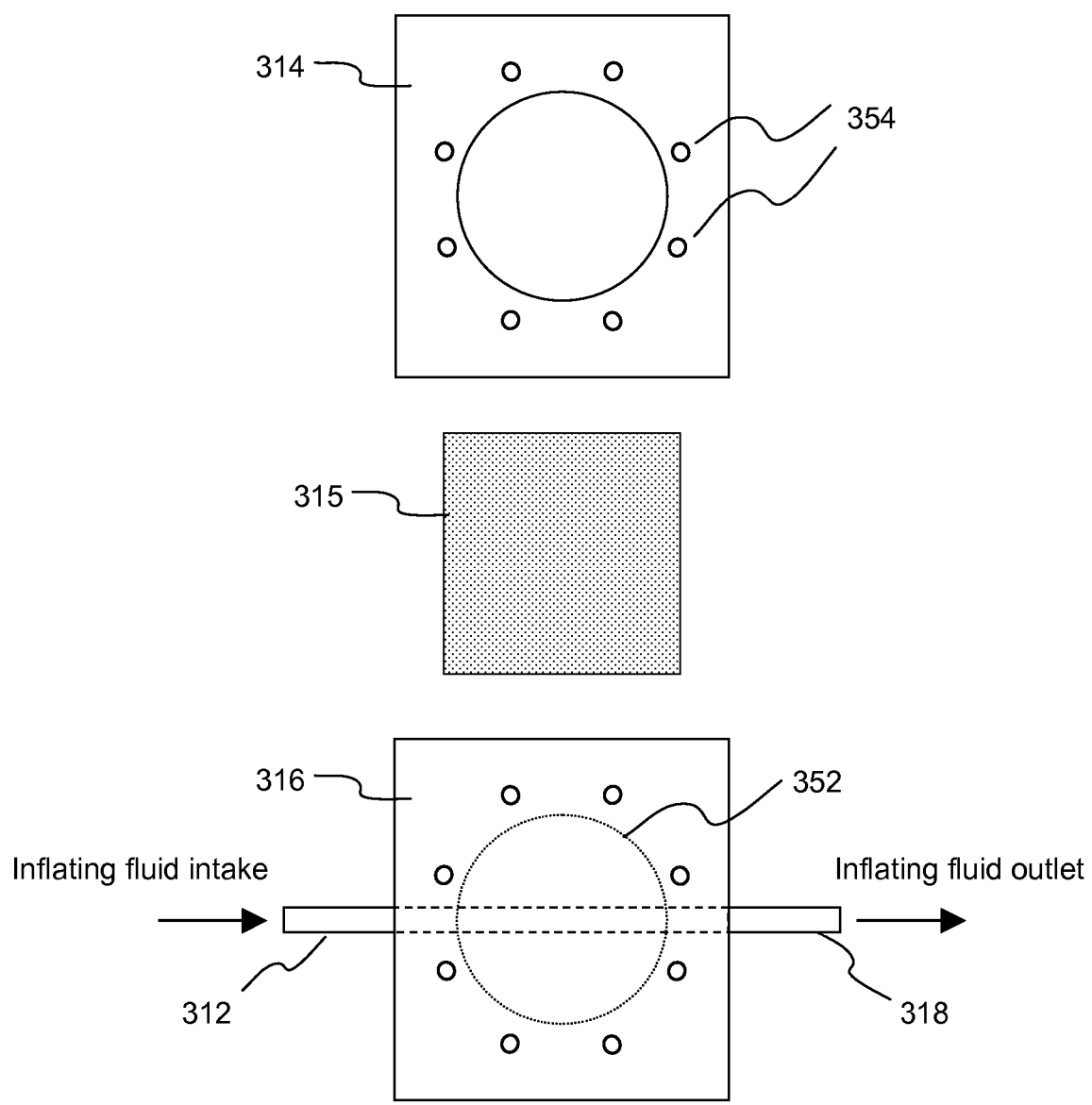
FIG. 3C is a diagram showing components of the first exemplary bi-axial test device of FIG. 3A in accordance with one embodiment of the present invention.

The plan view of the top plate 314, the bottom plate 316 and the elastomer membrane specimen 315 (virgin state) are shown in FIG. 3C, according to an embodiment of the present invention. To conduct the bi-axial test, the elastomer membrane specimen 315 is sandwiched between the top plate 314 and the bottom plate 316. The top and bottom plates are securely coupled together with a plurality of screws. Each of the screws (i.e., fasteners) is screwed in a pair of screw holes 354, one in the top plate, the other the bottom plate. The circular hole or opening is so dimensioned that the specimen 315 can be expanded with a relatively low pressure (e.g., maximum of 15 psi).

In order to create a fluid-tight requirement and non-slipping boundary condition of the membrane for the bi-axial test, an O-ring is used for sealing the perimeter of the circular hole or opening. In one embodiment, two O-rings 352 are located on the top side of the bottom plate 316, while one corresponding O-ring (not shown) is located on the bottom side of the top plate 314. The elastomer membrane specimen 315 is so dimensioned that the size is large enough to cover the circular hole of the top plate 314, and to be able to form a fluid-tight environment with the top and the bottom plates. The elastomer membrane specimen 315 has a uniform thickness such that the inflating fluids inflate the specimen 315 uniformly. It is noted that shape of the top and bottom plates, number of screws, type of screws and O-rings are not limited to the embodiment as shown in FIG. 3C. Other means that can achieve the same purpose of providing a fluid-tight test environment and non-slipping boundary condition of the membrane with a circular hole may be used for the present invention.

Further, the material properties of elastomers are temperature-dependent in general. Therefore the Mullins effect is also temperature-dependent. The first bi-axial test device 310, according to one embodiment of the present invention, is small enough such that the entire bi-axial test device 310 can be placed inside a water bath or an environment control chamber. The prior art approaches need huge specimen hence requiring huge temperature control facility.

Figure 3D:
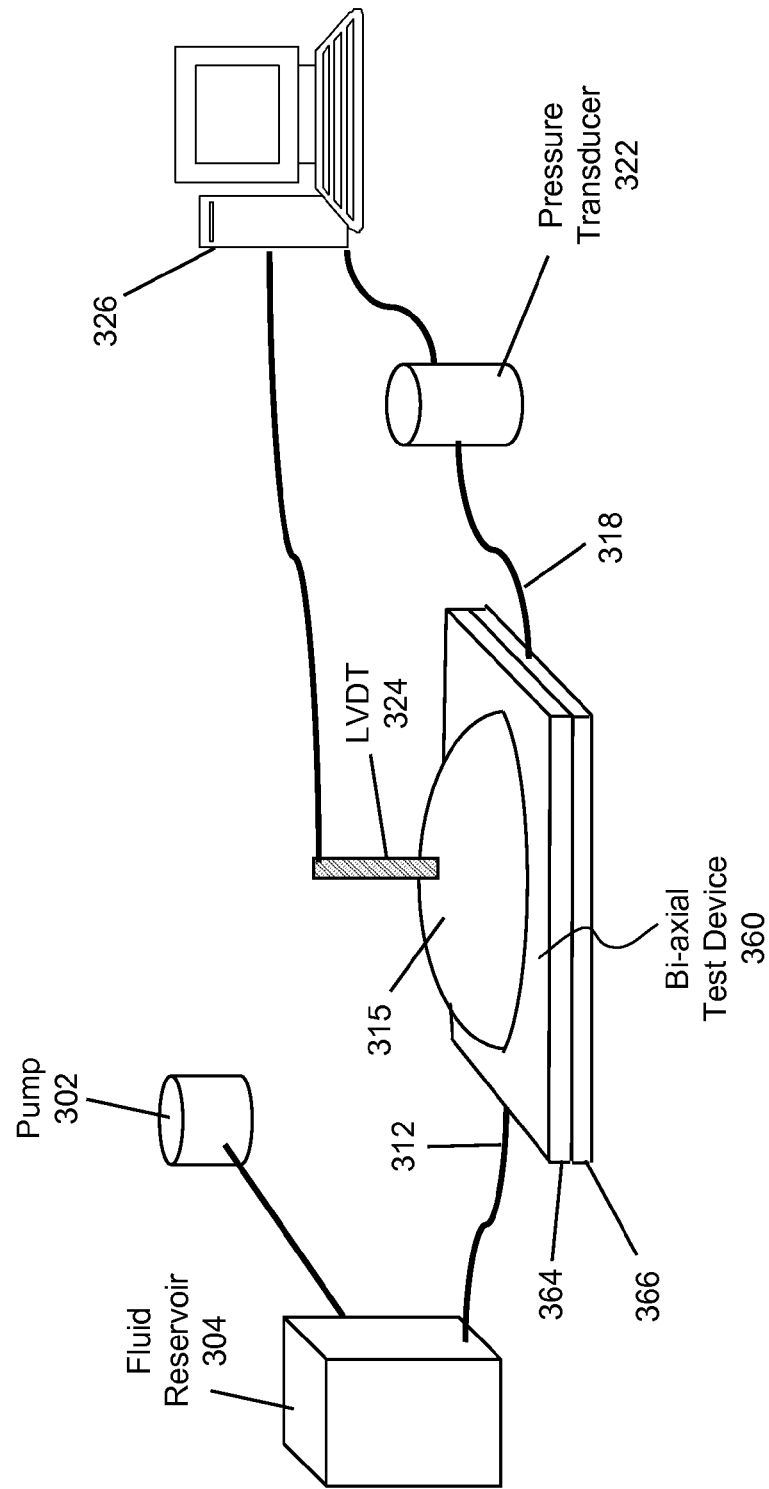
FIG. 3D is a diagram depicting another exemplary elastomer material properties determination system including a second exemplary bi-axial test device, according to another embodiment of the present invention.

Referring to FIG. 3D, a second exemplary bi-axial test device 360 is used in an elastomer material properties determination system 35, according to another embodiment of the present invention. Most of the components of the second bi-axial device 350 is the same as or substantially similar to those of the first bi-axial test device 310. The difference is that the second bi-axial test device 360 comprises a top plate 364 with an elliptical opening or hole. Because a circle is a special case of an ellipse, the second exemplary bi-axial test device 360 is a generic form of the first exemplary bi-axial test device 310. The other difference is locations of fastener holes 394 on the bottom plate 366, which is configured to pair with the top plate 364 as shown in FIG. 3F. The fastener holes 394 are located around the elliptical opening to ensure the O-ring 392 to provide a fluid-tight seal and non-slipping boundary condition of the membrane when the top and bottom plates are fastened together with a plurality of fasteners (e.g., screws) through a plurality of corresponding fastener holes 394.

Figure 3E:
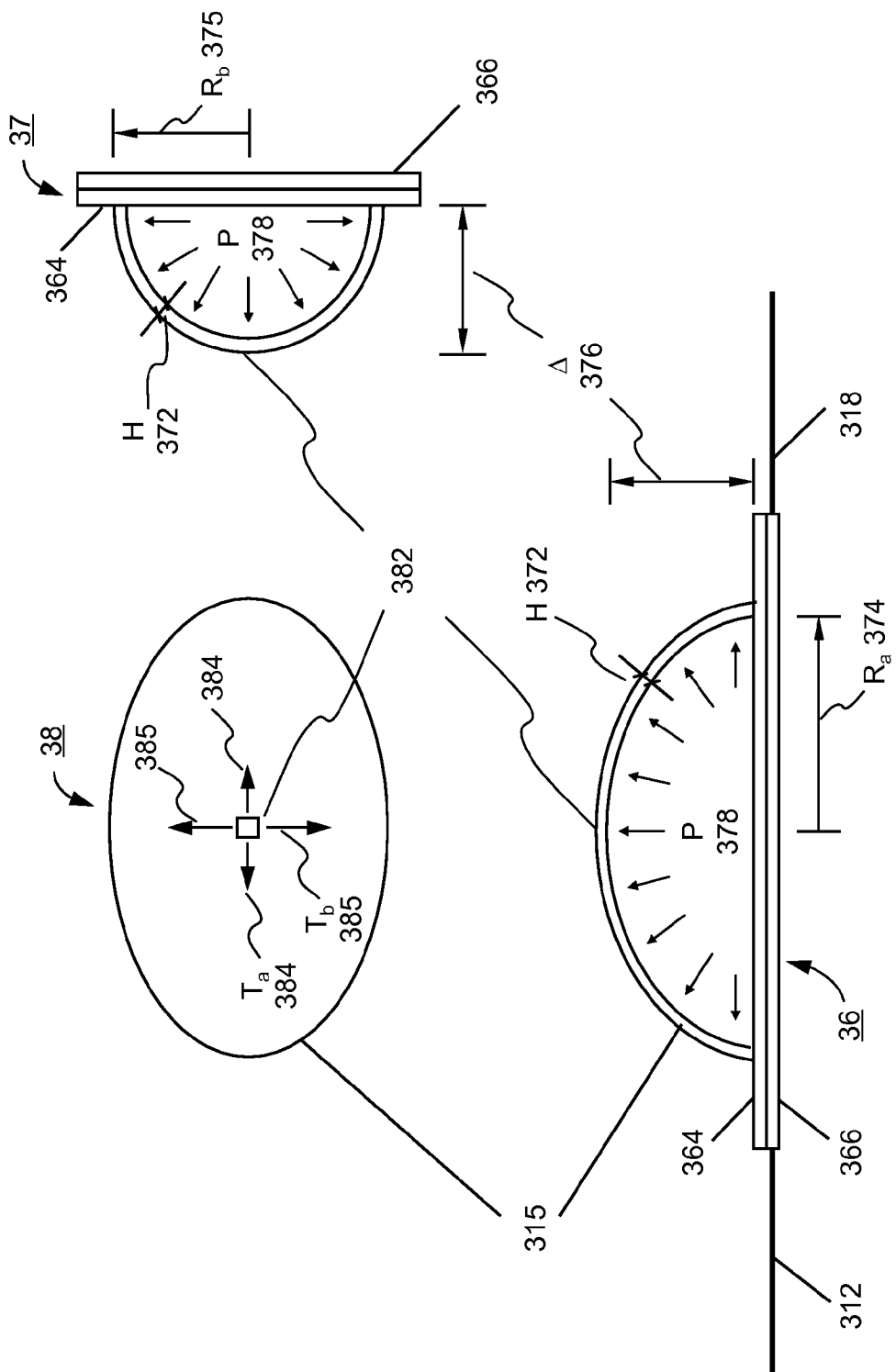
FIG. 3E is a diagram showing two lateral elevation views of the second exemplary bi-axial test device of FIG. 3D and a top plan view of the elastomer membrane specimen in accordance with one embodiment of the present invention.
Figure 3F:
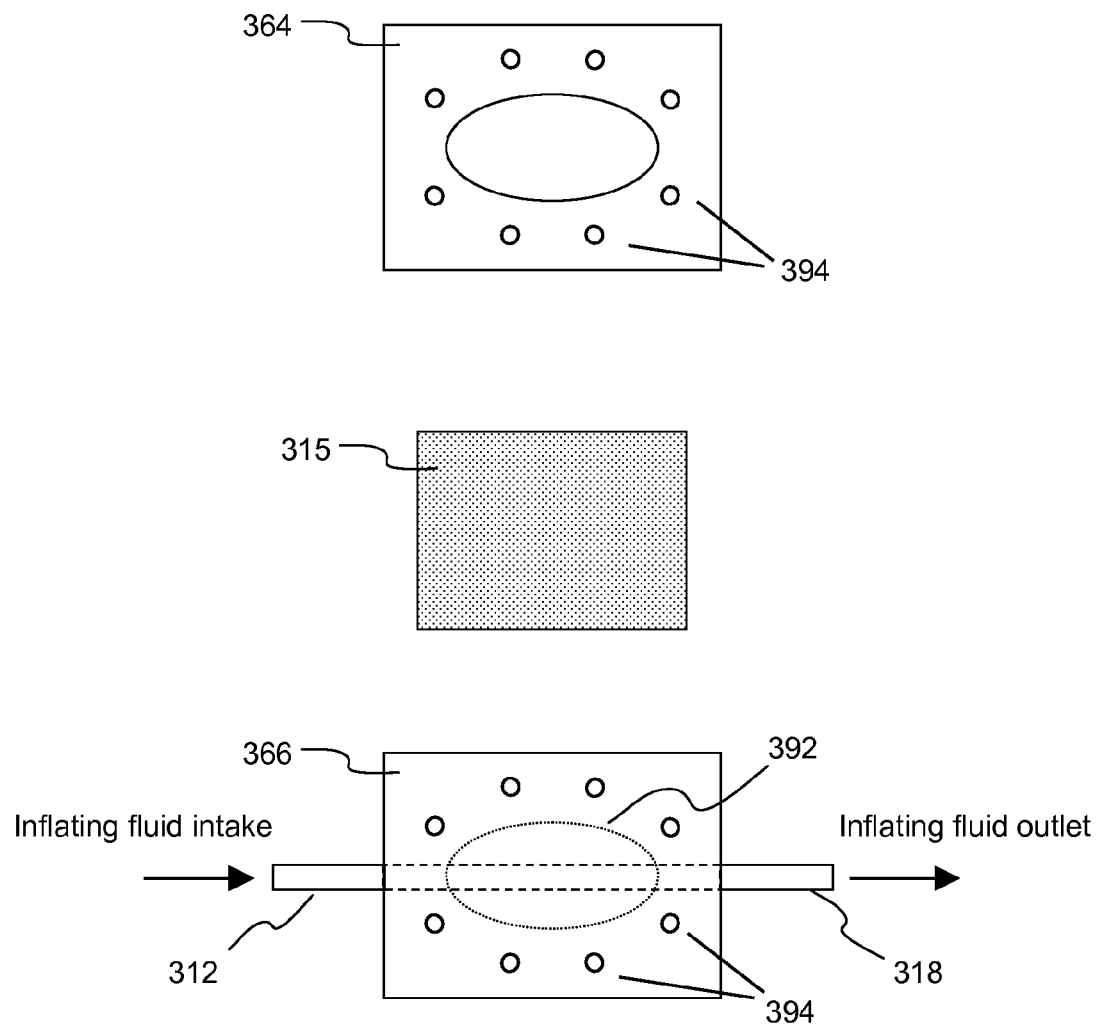
FIG. 3F is a diagram showing components of the second exemplary bi-axial test device of FIG. 3D, according to an embodiment of the present invention.

FIG. 3E shows two lateral elevation views 36 and 37, and a top view 38 of the second exemplary bi-axial device 360, according to one embodiment of the present invention. As described above, the opening of the top plate 364 has an elliptical shape that has two radii $R_a$ 374 and $R_b$ 375 for the major axis and the minor axis, respectively. The membrane specimen 315 with a uniform thickness H 372 is inflated by a pressure P 378 upward through the elliptical opening to a vertical displacement $\Delta$ 376 at the center 382 of the elliptical opening. The inflating fluids are pumped in from the inflating fluid intake 312 and the pressure is measured from the inflating fluid outlet 318 in the same manner used in the first exemplary bi-axial test device 310.

The major axis radius $R_a$ 374 is illustrated in the first lateral elevation view 36, while the minor axis radius $R_b$ 375 is shown in the second lateral elevation view 37. As shown in the top view 38, tensions $T_a$ 384 and $T_b$ 385 at the center 382 of the membrane specimen 315 may not be equal due to the elliptical opening. For small vertical displacement $\Delta$ 376, the relationship between the tensions and the radii is as follows:

$$\frac{T_a}{T_b} \cong \frac{R_b^2}{R_a^2}$$

The second bi-axial test device 360 enables a user to determine elastomer material properties under bi-axial tension with different ratios.

Figure 4A:
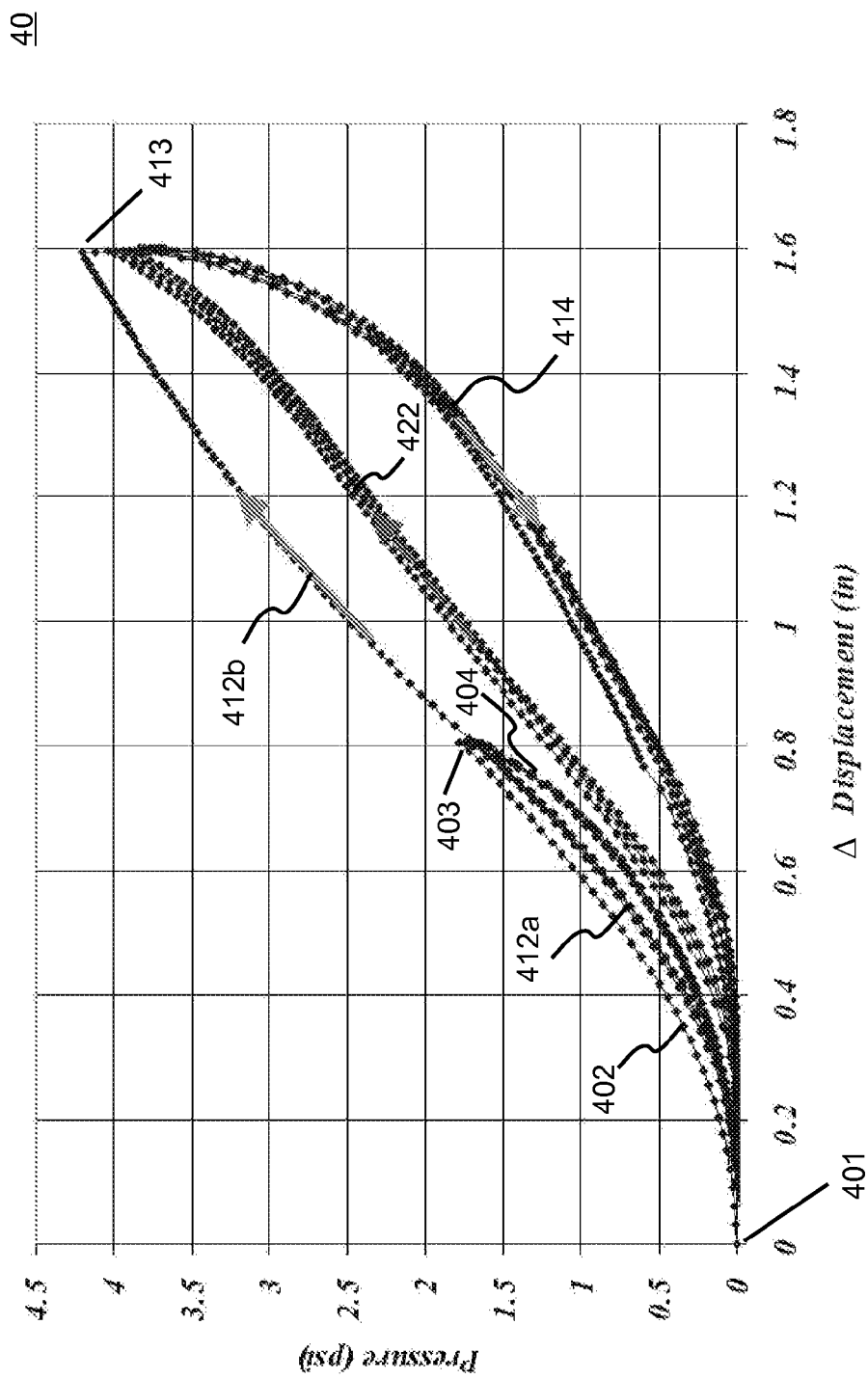
FIG. 4A is a diagram showing an exemplary pressure versus vertical displacement curves generated by the elastomer material properties determination system of FIG. 3A.

FIG. 4A shows an exemplary pressure versus vertical displacement (P-$\Delta$) curves 40 generated by the elastomer material properties determination system 30 of FIG. 3A. The vertical axis of the P-$\Delta$ curves 40 represents the pressure P 338, while the horizontal axis represents the vertical displacement $\Delta$ 336.

Using the elastomer material properties determination system 30, an elastomer membrane specimen 315 is inflated and measured. In the beginning of a bi-axial tension test, there is neither pressure nor displacement at 401. As more fluids are pumped into the first bi-axial test device 310, the displacement and the pressure increase accordingly following path 402 to reach a first pre-determined displacement (e.g., 0.8 inches) at 403. Then the specimen 315 is unloaded by reducing the pressure of the inflating fluids. The unloading phase following path 404 back to the original un-inflated state at 401. The specimen 315 is reloaded back to 403. The bi-axial tension test results show clearly that the reloading phase follows another path 412a, which is softer than the original loading phase path 402 but stiffer than the unloading path 404. Two more cycles of unloading and reloading of the specimen 315 are conducted thereafter.

Next, at 403 after three cycles of loading and reloading, the inflating fluids are increased to inflate the specimen 315 to a larger or second pre-determined vertical displacement (e.g., 1.6 inches) at 413 following path 412b. The path 412b is a path of loading specimen 315 in its virgin state again. The bi-axial tension test continues after that by repetitively unloading the specimen 315 to the original state 401 and reloading back to the second vertical displacement at 413. It is clear that the unloading phase follows path 414 and reloading phase follows path 422. The P-$\Delta$ curves 40 clearly demonstrate the Mullins effect, which includes a softer reloading path after the initial loading and reloading.

In order to use the measured data from the bi-axial tension test in a numerical analysis, a new constitutive equation is created to describe the elastomer behaviors for the Mullins effect demonstrated by the P-$\Delta$ curves 40 in FIG. 4A. The new constitutive equation (i.e., strain-energy density function) including Mullins effect damage function of an elastomer is defined as $\widetilde{W}(\lambda_i)$.

$$\widetilde{W}(\lambda_i) = \eta W(\lambda_i) \tag{1}$$

where $W(\lambda_i)$ is the strain-energy density function based on the initial loading (i.e., virgin state), $\eta$ is a damage function for the Mullins effect, and $\lambda_i$ is the stretch ratio of the elastomer.

| For initial loading | $\eta = 1$ | (2a) |
|---|---|---|
| For unloading | $\eta = 1 - \frac{1}{r_1}\tanh\left[\frac{1}{m_1}(W_m - W)\right]$ | (2b) |
| For subsequent reloading | $\eta = 1 - \frac{1}{r_2}\tanh\left[\frac{1}{m_2}(W_m - W)\right]$ | (2c) |

$W_m(\lambda_i)$ is the previous maximum of the strain-energy density function before unloading (e.g., 403 and 413 of FIG. 4A). $r_1$, $r_2$, $m_1$ and $m_2$ are the material constants for Mullins effect damage function. With the Mullins effect damage function, the loading 402, 412b, unloading 404, 414 and subsequent reloading 412a, 422 follow different paths as shown in FIG. 4A. It is noted that the material constants, $r_1$ and $r_2$, are greater than one in general.

Generally, the strain-energy function $W(\lambda_i)$ may be in one of the many material model forms, for example, neo-Hookean, Mooney, Ogden incompressible or Ogden compressible. When Ogden compressible material model is considered, all others are special cases. For highly compressible materials the strain-energy density for Ogden constitutive equation can be written as follows:

$$W = \sum_{j=1}^{m} \frac{C_j}{b_j}\left[\lambda_1^{b_j} + \lambda_2^{b_j} + \lambda_3^{b_j} - 3 + \frac{1}{n}(J^{-nb_j} - 1)\right] \tag{3}$$

where $C_j$, $b_j$ and n are material constants, $J = \lambda_1 \lambda_2 \lambda_3$ represents the ratio of deformed to un-deformed volume, and $\lambda_1$, $\lambda_2$ and $\lambda_3$ are stretch ratios of the elastomer in three orthogonal directions, respectively. When n=$\infty$, Equation (3) becomes the Ogden incompressible material model. When n=$\infty$, m=2, $b_1$=2 and $b_2$=−2, Equation (3) becomes the Mooney material model. When n=$\infty$, m=1 and $b_1$=2, Equation (3) becomes the neo-Hookean material model.

According to one embodiment of the present invention, the neo-Hookean material model is used to demonstrate how material constants, $r_1, r_2, m_1$ and $m_2$, are determined from the measured data of the bi-axial tension test. The strain-energy function for the neo-Hookean material model is listed as follows:

$$W(\lambda_i) = C_1(\lambda_1^2 + \lambda_2^2 + \lambda_3^2 - 3) \tag{4}$$

An approximate relationship between the inflating pressure P 338 and the deformation at the pole $\Delta$ 336 can be obtained as follows:

$$P = \frac{2C_1 H}{R}\left\{\frac{1}{\left(\frac{\Delta}{R}+\frac{R}{\Delta}\right)}\left[1-\frac{1}{\lambda^6}\right]\right\} \tag{5}$$

Figure 4B:
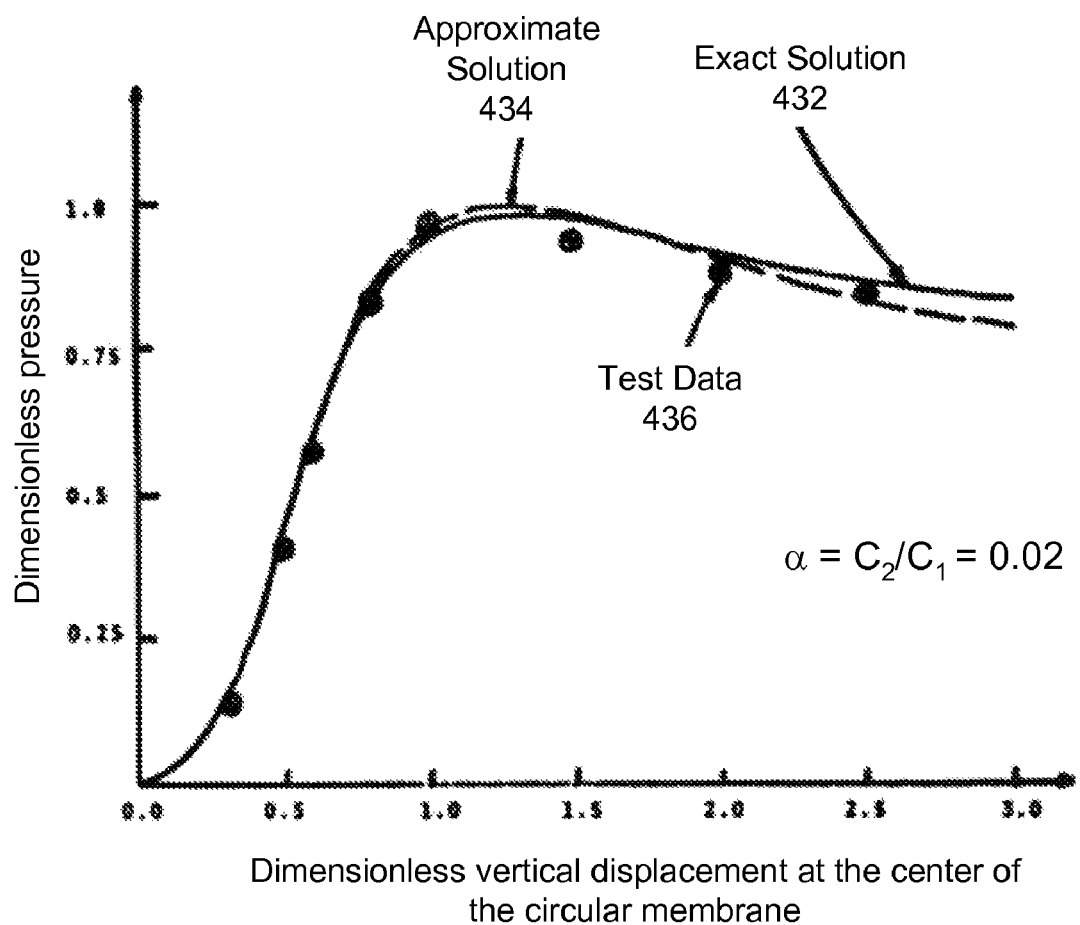
FIG. 4B is a diagram showing the comparison between exact solution, approximate solution and test data of inflating a circular elastomer membrane based on Mooney material model.

The relationship between $\lambda$ and $\Delta$ is $$\lambda = \frac{\left(\frac{\Delta}{R}+\frac{R}{\Delta}\right)}{2}\sin^{-1}\left(\frac{2}{\left(\frac{\Delta}{R}+\frac{R}{\Delta}\right)}\right) \tag{6}$$

Where $\lambda$ is the stretch ratio of the elastomer in the planar direction, R 334 is the radius of the circular membrane (e.g., elastomer specimen 315) and H 332 is the thickness of the circular membrane. Similar expression may be obtained for Mooney material model and other constitutive equations. The exact numerical solution 432, approximate solution 434 obtained from Equations (5) and (6), and test data 436 for inflating a circular thin disk (e.g., elastomer specimen 315) are compared and plotted in FIG. 4B. It is shown that the approximate solution 434 from Equations (5) and (6) represents a very good correlation to the true solution 432 and measured test data 436. It is noted that the material used in FIG. 4B is for Mooney material model with $\alpha=C_2/C_1=0.02$.

When the Mullins effect damage function is considered, Equation (5) becomes $$P = \frac{2C_1 H}{R}\left\{\frac{1}{\left(\frac{\Delta}{R}+\frac{R}{\Delta}\right)}\left[1-\frac{1}{\lambda^6}\right]\right\}*\eta \tag{7}$$

Using the measured data from the bi-axial tension test and Equation (7), the material constants in Equations (2b) and (2c) can be obtained. The first set of material constants, $r_1$ and $m_1$, are obtained from the pressure-deformation unloading curve (e.g., path 404 or 414 of FIG. 4A). The second set of material constants, $r_2$ and $m_2$, are obtained from the pressure-deformation reloading curve (path 412a or 422 of FIG. 4A). These constants are all obtained from the least-square curve fit. Equations 2(a), 2(b) and 2(c) can be applied to one-, two- and three-dimensional analyses of structures containing elastomers tested.

Figure 4C:
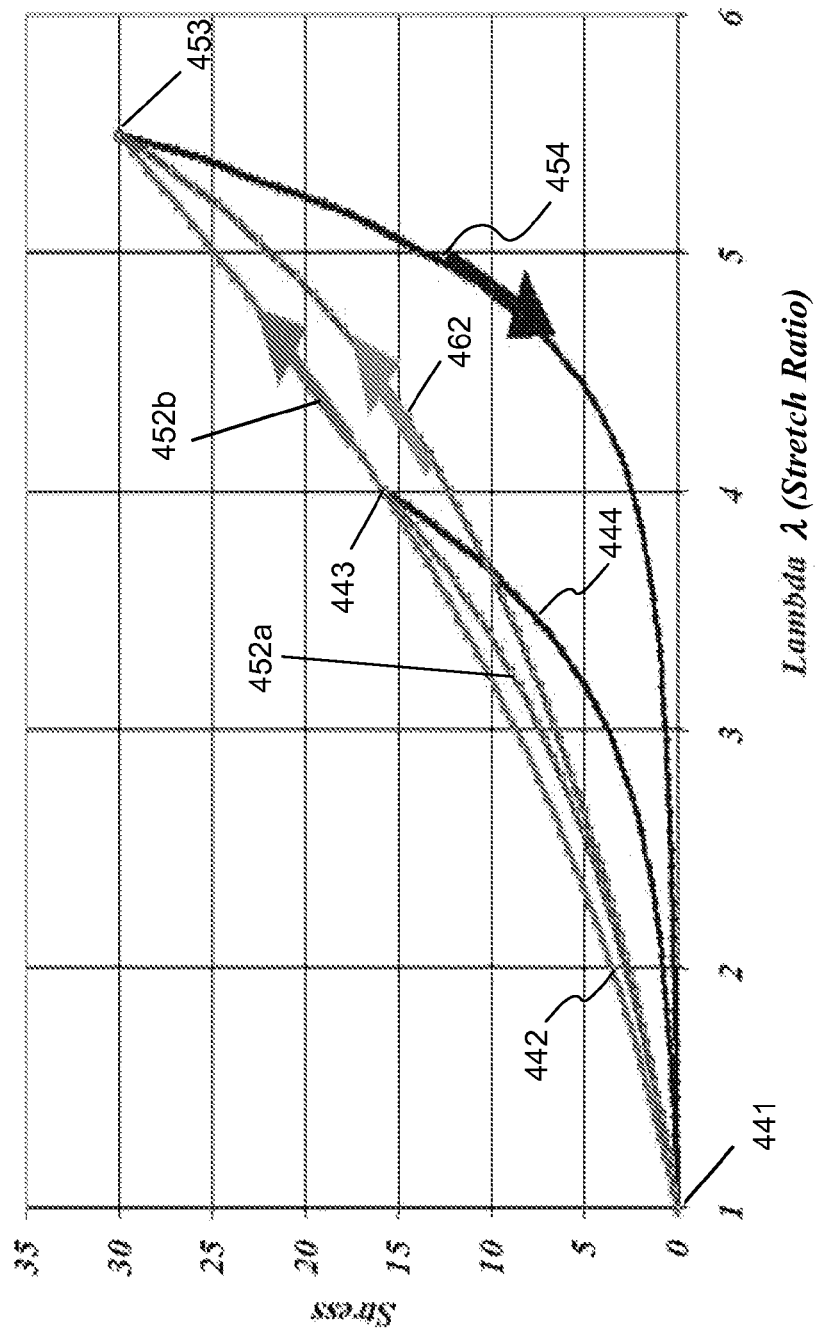
FIG. 4C is a diagram illustrating a stress-stretch ratio relationship (curves) of an elastomer under load-unload-reload phases calculated using a new constitutive equation in accordance with one embodiment of the present invention.

Referring to FIG. 4C, which shows stress-stretch ratio ($\sigma$-$\lambda$) curves 42 based on Equations (2a), (2b) and (2c) in accordance with one embodiment of the present invention. The $\sigma$-$\lambda$ curves 42 show similar behaviors with the measured test data (i.e., P-$\Delta$ curves 40) as shown in FIG. 4A. The initial stress $\sigma$ and the initial stretch ratio $\lambda$ (i.e., un-stretched state) start at the origin 441. A loading path 442 leads to a state 443. The stress $\sigma$ follows a first unloading path 444 back to the origin 441. Reloading phase follows paths 452a and 452b to reach another state 453. Then the stress $\sigma$ follows a second unloading path 454 to the origin 441. The subsequent reloading phase follows path 462. The similarity of the curves 42 and the P-$\Delta$ curves 40 validates the usage of Equations (2a), (2b) and (2c) to numerically analyze elastomers.

Although elastomer material property data from a bi-axial tension test for the second exemplary bi-axial test device 360 is not shown, the test data would show substantial similar characteristics for the Mullins effect as shown in FIG. 4A. All of the test procedures described herein for the first exemplary bi-axial test device 310 applies to the second bi-axial test device 360. With the second bi-axial test device 360, the user can conduct elastomer material properties test with different aspect ratios (i.e., bi-axial tension with different ratios in two planar directions).

The constitutive equation for a material (e.g., an elastomer) needs to reflect the experimental results (i.e., material properties) obtained in a material property test (e.g., a bi-axial test using the second exemplary bi-axial test device with an elliptical opening). The constitutive equation representing material behaviors of elastomer is highly non-linear hence the unknown coefficients of the constitutive equation need to be determined in a trial-and-error methodology. One of the procedures in determining the unknown coefficients is to use optimization software. First, a finite element analysis model of an elliptical membrane specimen is created to simulate the bi-axial test with the elliptical opening. Next, a finite element analysis of inflating the membrane specimen is performed using an initial set of guessed values of the unknown coefficients. The analysis results are compared with the experimental or test data. When the discrepancy is larger than an acceptable pre-defined threshold, another set of guessed values of the unknown coefficients are used for performing the simulation again. The trial-and-error procedure continues until the analysis results and the test data are within the threshold.

The tedious trial-and-error method may be automated with the advanced numerical software such as an engineering design optimization software program. With the appropriate material model, one can use a combination of finite element analysis software, optimization software and the experimental test data, P-$\Delta$ curve to determine the material constants of the inflation of an elliptical membrane. One such engineering design optimization software is LS-OPT® from Livermore Software Technology Corporation, Livermore, Calif.

Figure 5A:
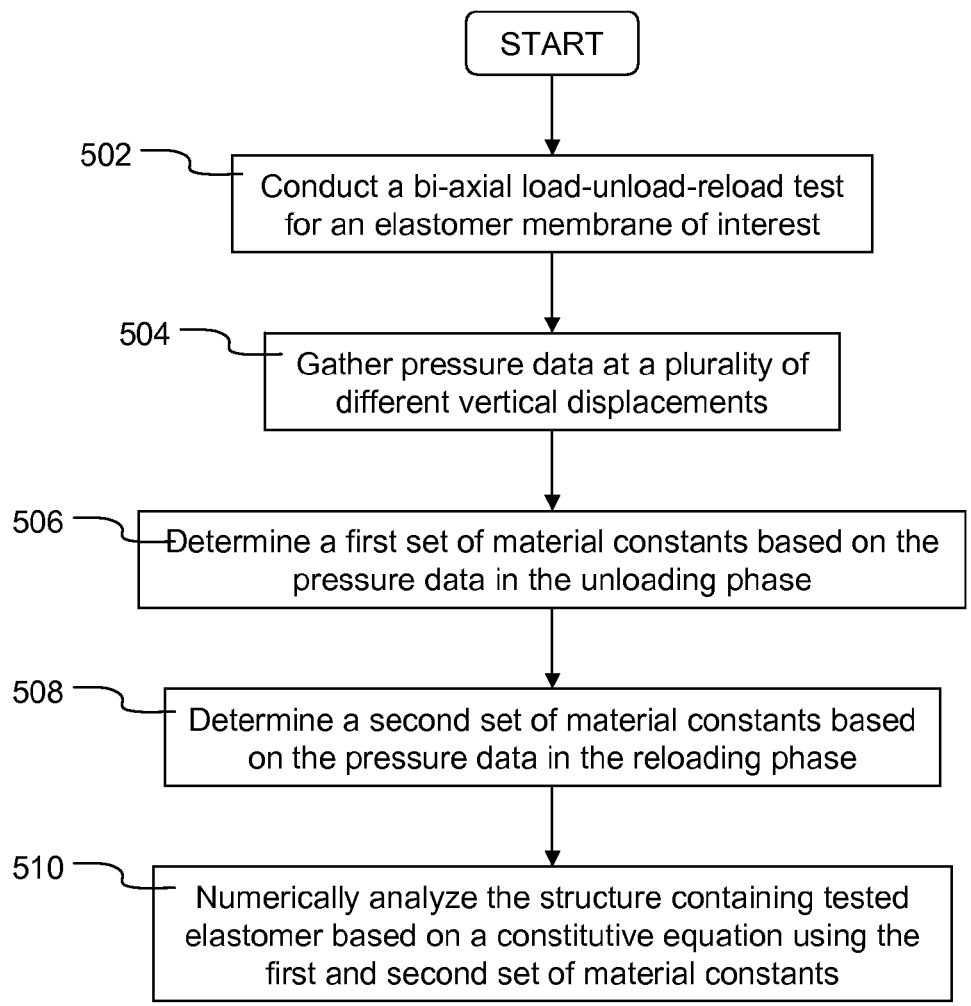
FIG. 5A is a flowchart showing the process of numerically analyzing a structural product containing elastomer with the material properties obtained from a bi-axial test using the first exemplary bi-axial test device of FIG. 3A, according to an embodiment of the present invention.

FIG. 5A is a flowchart illustrating a process 50 for numerically analyzing structure containing elastomer with the material properties obtained from a bi-axial tension test using the first bi-axial test device of FIG. 3A, according to an embodiment of the present invention. The process 50 is preferably understood in conjunction with the previous figures especially FIG. 3A and FIG. 4A, and the process 50 is preferably implemented in software.

The process 50 starts, at 502, by conducting the bi-axial tension test of an elastomer membrane specimen 315 of interest using an elastomer material properties determination system (e.g., system 30). Pressure versus vertical displacement data are measured and gathered following a load-unload-reload test (i.e., bi-axial tension test) described in FIG. 4A at 504. Using the geometry of the elastomer membrane specimen 315 (i.e., radius R 334 and thickness H 332), a first set of the material constants, $r_1$ and $m_1$, of Equation 2(b) are determined at 506. The determination is based on the measured data in the unloading phase (e.g., path 404 or 414 of FIG. 4A) using a least square fit technique. Similarly, a second set of material constants, $r_2$ and $m_2$, of Equation 2(c) are determined at 508. The difference is that the measured data in the reloading phase (e.g., path 412a or 422 of FIG. 4A) are used. After both the first set and the second set of material constants are determined, at 510, any structure containing the elastomer of interest (i.e., the tested elastomer at 502) can be numerically analyzed using constitutive equations (e.g., Equations 2(a), 2(b) and 2(c)). One implementation of this technique is to include the constitutive equation in a finite element analysis program, such that the user can model the structure with finite element with material properties defined by Equations 2(a)-2(c) with the first and second set of material constants defined automatically by the application program or manually by users.

Figure 5B:
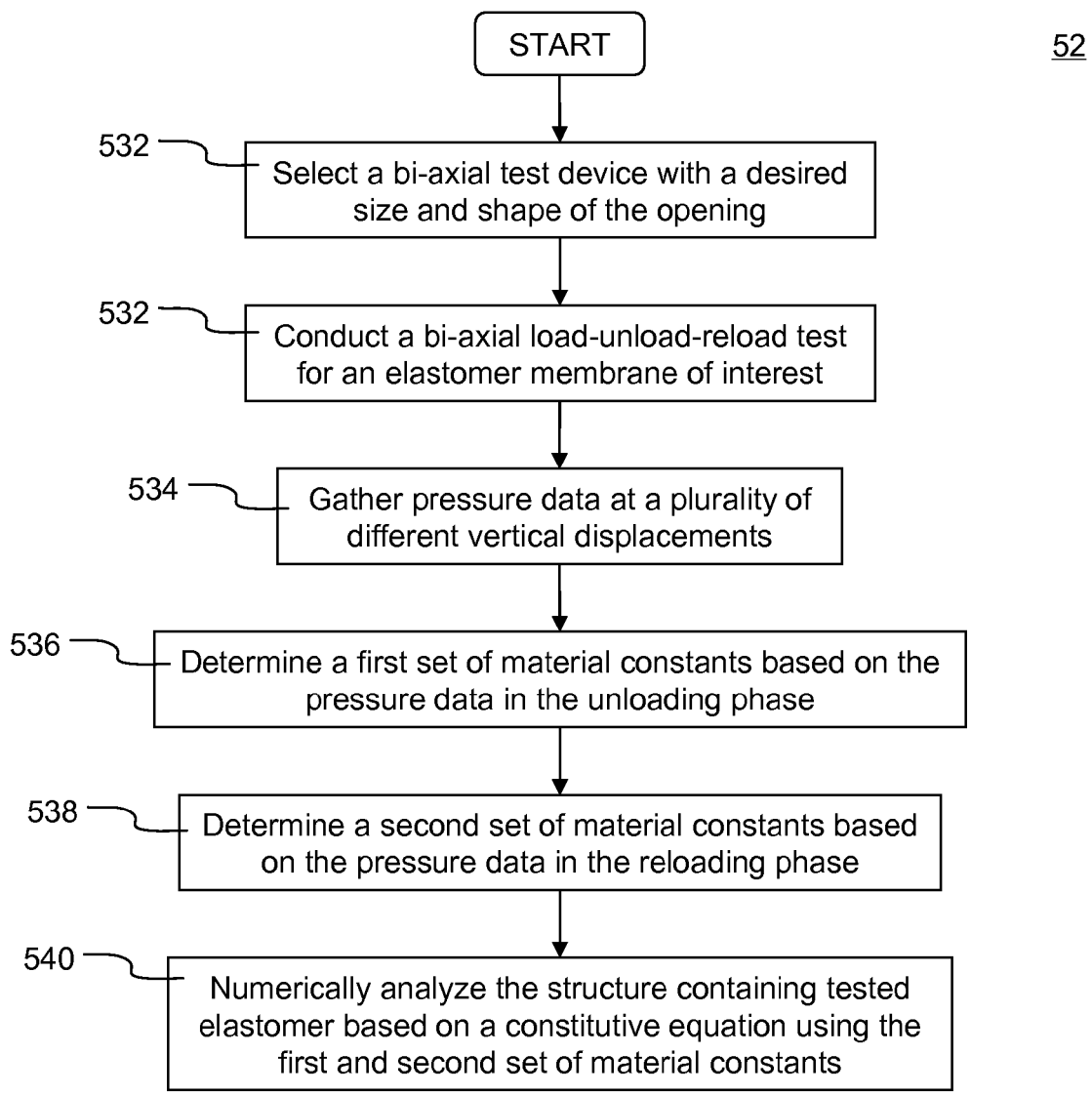
FIG. 5B is a flowchart illustrating the process of numerically analyzing a structure product containing elastomer with the material properties obtained in a bi-axial test using the second exemplary bi-axial test device of FIG. 3D, according to another embodiment of the present invention.

Referring to FIG. 5B, which is a flowchart illustrating a process 52 of numerically simulating a structural product (e.g., automobile) containing elastomer with material properties obtained in a bi-axial tension test using the second bi-axial test device of FIG. 3D, according to another embodiment of the present invention. The process 52 is substantially similar to the process 50. The difference is that the process 52 starts with a selection of bi-axial test device with a desired size and shape of the opening at 531. For example, an elliptical opening with a ratio of 2:1 or other ratios between the major axis radius and the minor axis radius may be chosen to conduct the bi-axial tension test to determine material properties of elastomer. The rest of the process 52 (i.e., steps 532-540) is the same as the steps 502-510 of the process 50. Because there is no close form solution to estimate the material constants for the elliptical opening, the material constants can only be determined by an iterative optimization process.

The methods or algorithms described in connection with the embodiments disclosed herein may be embodied directly in hardware, in a software module executable by a processor, or in a combination of both, in the form of control logic, programming instructions, or other directions, and may be contained in a single device or distributed across multiple devices. A software module may reside in Random Access Memory (RAM), flash memory, Read-Only Memory (ROM), Erasable Programmable Read-Only Memory (EPROM), Electronically Erasable Programmable Read-Only Memory (EEPROM), registers, hard disk, a removable disk, Compact Disc Read-Only Memory (CD-ROM), Digital Video Disc (DVD) or any other form of storage medium known in the art. A storage medium may be coupled to the processor such that the processor can read information from, and write information to, the storage medium. In the alternative, the storage medium may be integral to the processor.

Although the present invention has been described with reference to specific embodiments thereof, these embodiments are merely illustrative, and not restrictive of, the present invention. Various modifications or changes to the specifically disclosed exemplary embodiments will be suggested to persons skilled in the art. For example, whereas the exemplary bi-axial test devices have been shown and described to determine the material properties of elastomers, other types of rubber-like material may be determined. Whereas the LVDT has been described and shown to measure the vertical displacement of the elastomer membrane, other types of measurement device may also be used instead. Whereas the pressure transducer has been shown and described to measure the pressure in the exemplary bi-axial test devices, other types of pressure gauge may be used. In summary, the scope of the invention should not be restricted to the specific exemplary embodiments disclosed herein, and all modifications that are readily suggested to those of ordinary skill in the art should be included within the spirit and purview of this application and scope of the appended claims.

What is claimed is:

1. A device for determining elastomer material properties for the Mullins effect under bi-axial tension, the device comprising:
    a top plate having an elliptical opening;
    a bottom plate having an inflating fluid intake and an inflating fluid outlet;
    a plurality of fasteners for coupling the top and bottom plate;
    an elastomer specimen configured to be sandwiched between the top and bottom plate; wherein the elastomer specimen's area is larder enough to cover the opening so that a fluid-tight environment and non-slipping boundary condition of the membrane are formed when the top plate and the bottom plate are coupled together by the fasteners, wherein the fluid-tight environment further includes one first O-ring fixedly attached to bottom of the top plate and two second O-rings fixedly attached to top of the bottom plate, around the opening's perimeter, the first O-ring fits in between the two second O-rings.

2. The device of claim 1, wherein the elliptical opening has a major axis radius and a minor axis radius.

3. The device of claim 2, wherein the elastomer specimen is an elastomer membrane with uniform thickness.

4. The device of claim 3, wherein the elastomer specimen is configured to be expanded upwards through the opening by pressure of inflating fluids.

5. The device of claim 3, wherein the center of the elastomer membrane is under two orthogonal planar tension forces when the inflating fluids are pumped into the device.

6. The device of claim 5, wherein ratio of the two orthogonal planar tension forces is a function of the major axis radius and the minor axis radius.

7. The device of claim 1, wherein the fasteners are screws.

8. A device for determining elastomer material properties for the Mullins effect under bi-axial tension, the device comprising:
    a top plate having an elliptical opening;
    a bottom plate having an inflating fluid intake and an inflating fluid outlet;
    a plurality of fasteners for coupling the top and bottom plate;
    an elastomer specimen configured to be sandwiched between the top and bottom plate;
    wherein the elastomer specimen's area is larger enough to cover the opening so that a fluid-tight environment and non-slipping boundary condition of the membrane are formed when the top plate and the bottom plate are coupled together by the fasteners, wherein the fluid-tight environment further includes two first O-rings fixedly attached to bottom of the top plate and one second O-ring fixedly attached to top of the bottom plate, around the opening's perimeter, the second O-ring fits in between the two first O-rings.

9. The device of claim 8, wherein the elliptical opening has a major axis radius and a minor axis radius.

10. The device of claim 9, wherein the elastomer specimen is an elastomer membrane with uniform thickness.

11. The device of claim 10, wherein the elastomer specimen is configured to be expanded upwards through the opening by pressure of inflating fluids.

12. The device of claim 10, wherein the center of the elastomer membrane is under two orthogonal planar tension forces when the inflating fluids are pumped into the device.

13. The device of claim 12, wherein ratio of the two orthogonal planar tension forces is a function of the major axis radius and the minor axis radius.

14. The device of claim 8, wherein the fasteners are screws.

15. A system for determining elastomer material properties for the Mullins effect under bi-axial tension, the system comprising:

a bi-axial test device having a top plate having an elliptical opening, a bottom plate, a plurality of connector means for coupling the top and bottom plate, an inflating fluid intake and an inflating fluid outlet, the inflating fluid intake and the inflating fluid outlet are operable coupling to the bottom plate, whereby an elastomer specimen is configured to be sandwiched between the top and bottom plates;

a fluid reservoir, coupling to the inflating fluid intake, configured to store inflating fluids;

a pump, coupling to the fluid reservoir, configured to control the inflating fluids;

a linear variable differential transformer (LVDT) configured to measure vertical displacement at the center of an elastomer membrane specimen placed in the bi-axial test device;

a pressure transducer, coupling to the inflating fluid outlet configured to measure pressure of the inflating fluids; and a computer, coupling to the LVDT and the pressure transducer, configured to gather and plot the measured pressure and vertical displacement throughout the bi-axial test.

* * * * *